United States Patent
Grossi et al.

[11] Patent Number: 6,033,400
[45] Date of Patent: Mar. 7, 2000

[54] SHAPED ELECTRODE FOR A RESECTOSCOPE

[75] Inventors: Benedetto Grossi, Stamford, Conn.; Robert H. Quint, Jamaica; Richard P. Muller, Bronx, both of N.Y.

[73] Assignee: Circon Corporation, Santa Barbara, Calif.

[21] Appl. No.: 08/800,488

[22] Filed: Feb. 14, 1997

Related U.S. Application Data

[60] Provisional application No. 60/015,668, Apr. 19, 1996.

[51] Int. Cl.$^7$ ................................................. A61B 17/39
[52] U.S. Cl. ............................... 606/41; 606/45; 606/46; 606/49
[58] Field of Search ................................. 606/41, 45, 46, 606/49

[56] References Cited

U.S. PATENT DOCUMENTS

| | | |
|---|---|---|
| 642,849 | 2/1900 | Otto . |
| 3,835,842 | 9/1974 | Iglesias ........................................ 128/7 |
| 4,095,601 | 6/1978 | Aufrang ................................... 128/405 |
| 4,314,559 | 2/1982 | Allen ....................................... 128/303 |
| 4,532,924 | 8/1985 | Auth et al. .......................... 128/303.17 |
| 4,765,331 | 8/1988 | Petruzzi et al. .................... 128/303.14 |
| 4,917,082 | 4/1990 | Grossi et al. ............................. 606/46 |
| 5,354,296 | 10/1994 | Turkel ....................................... 606/49 |
| 5,395,363 | 3/1995 | Billing et al. ............................. 606/41 |
| 5,569,244 | 10/1996 | Hahnen .................................... 606/46 |
| 5,582,610 | 12/1996 | Grossi et al. ............................. 606/46 |
| 5,782,829 | 7/1998 | Swiantek et al. ......................... 606/46 |

FOREIGN PATENT DOCUMENTS 253911  2/1988  U.S.S.R. ................................. 606/50

OTHER PUBLICATIONS

Use of the Resectoscope in Gynecology by Richard A. Auhll, pp. 91–99, Oct. 11, 1990, Biomedical Business International.

Transurethral Evaporization of Prostrate (Turp) With Nd:Yag Laser Using Contact Free Beam Technique: Results in 61 Patients with Benign Prostatic Hyperplasia by Peby Perinchery Narayan, M.D., George Fournier, M.D., R. Indudhara, M.D., R. Leidich, M.D., K. Shinohara, M.D. and Alex Ingermann, M.D. pp. 813–820, Jun., 1994, vol. 43, No. 6, Issue of Urology.

Transurethral Vaporizaton of the Prostate (T.V.P.): New Horizons by Irving M. Bush, M.D., Edward Malters, M.D. and Jan Bush, R.N.

Operating Manual, McCarthy Surgical Unit Type 504A, Comprex Oscillator Corporation.

*Primary Examiner*—Lee Cohen
*Attorney, Agent, or Firm*—Bradley M. Ganz

[57] ABSTRACT

A shaped conductive core electrode member having an elongated curved sharp leading cutting edge forming part thereof for use with a resectoscope is shown. The electrode includes an electrode lead member having an elongated conductor member having a first end and a second end with an insulative cover extended therebetween. The first end has a protruding electrode adapted to be electrically connected to an electrosurgical generator. The second end terminates in an electrode support member which is operatively connected to or forms an integral part of the shaped electrode as an active member. The electrode support member has an elongated semi-rigid bifurcated arm terminating in a conductive core. The bifurcated arm is covered with an insulative material except at the distal end where the shaped electrode is located. The electrode support member includes the shaped electrode having a sharp leading cutting edge and an opening extending therethrough for rigidly operatively mounting the shaped conductive core electrode member on the conductive core of the support member. The shaped conductive core electrode member may have openings and/or ridges or grooves formed in the side wall portion thereof. A method for incising and vaporizing tissue, such as prostate tissue and bladder tumors, using the shaped electrode for a resectoscope is also shown.

25 Claims, 6 Drawing Sheets

Parameters For Vaporization

| VOLTAGE | MEDIUM | EFFECT |
|---|---|---|
| 200 V | AIR | CUT |
| 300 V | LIQUID | CUT |
| 300 V | AIR | CHARRING |
| 400V TO ABOUT 500V | LIQUID | CHARRING |

SHAPED ELECTRODE FOR A RESECTOSCOPE

RELATED APPLICATION

This Application claims the benefit, under Title 35, United States Code §119(e), of U.S. Provisional patent application Ser. No.: 60/015,668 filed Apr. 19, 1996.

BACKGROUND OF THE INVENTION

1. Field of the Invention

The invention relates generally to an electrode having a rigidly mounted electrode element adapted for use with an endoscope for tissue resection, coagulation, and ablation and more particularly relates to an electrode having a shaped conductive core electrode member having a sharp leading cutting edge for use in performing procedures, such as, for example, in the genitourinary tract on soft tissue, including bladder and prostate, for BPH procedures, for hemostasis, incision, excision and ablation or in performing other surgical procedures requiring removal or ablation of tissue.

2. Description of the Prior Art

Use of resectoscopes to treat tissue in the genitourinary tract is well known. Typical of such resectoscopes are the devices disclosed in U.S. Pat. Nos. 5,151,101 and 4,955,884.

Resectoscopes used for transurethral resection of the prostate (TURP) have four elements, a resectoscope sheath, sometimes referred to as a sheath or an outer sheath, a working element, an electrode and a telescope. The electrodes are operatively connected to a working element and a telescope is slideably inserted through the working element and into position along side of the electrode. Certain electrodes include an electrode stabilizer which is adapted to receive the telescope. The so assembled working element, telescope and electrode are removably inserted into the sheath to perform a procedure.

In a typical urological procedure, the sheath with its obturator, is passed through the urethra to the vicinity of the prostate and/or bladder neck. The obturator is then removed and the resectoscope working element with a telescope and electrode assembled thereto is inserted into the sheath. The electrode, which is also known as a resectoscope electrode, is typically in the form of a cutting loop located at the distal end of an electrode lead member.

An electrosurgical current, which may be either a coagulation current, a cutting current or some blend thereof is applied to the cutting loop. The energized cutting loop is moved through the prostatic tissue and cuts the tissue being treated. The cutting loop can also be used to coagulate the severed vessels in the tissue. In urological procedures, under water, the peak voltage of the electrosurgical cutting currents are typically in the range of 200 volts to about 500 volts at a power level of between about 100 watts to about 300 watts.

A resectoscope electrode having a stabilized cutting loop for a resectoscope is described in U.S. Pat. No. 4,917,082.

The resectoscope electrode described in U.S. Pat. No. 4,917,082 is adapted for use with a urological endoscope or resectoscope. The electrode comprises an electrode lead, an electrode end and an electrode stabilizer. U.S. Pat. No. 4,917,082 discloses that the electrode may take the form of a coagulating electrode, knife electrode, retrograde knife electrode, punctate electrode or roller electrode having a smooth exterior surface.

Continuous flow resectoscopes which utilize a cutting loop electrode for urological procedures are well known in the art and an example of a continuous flow resectoscope is disclosed in U.S. Pat. No. 3,835,842.

An article entitled "THE USE OF THE RESECTOSCOPE IN GYNECOLOGY" by Richard A. Auhll which appeared at pages 91 through 99 of the Oct. 11, 1990 issue of Biomedical Business International (the "Auhll Reference") disclosed the use of a uterine resectoscope system in the form of a continuous flow resectoscope using an electrosurgical electrode for performing intrauterine procedures.

The Auhll Reference discussed three electrode structures, namely: (1) an electrosurgical cutting loop to treat fibroid tissues; (2) a roller ball having a smooth exterior surface for endometrial ablation (which is cauterization of the endometrium); and (3) electrosurgical needle to cut through and destroy tissue producing intrauterine synechia. In gynecological procedures, the voltage of the electrosurgical cutting currents are typically in the range of 200 volts to about 400 volts at a power level of between 60 watts and 200 watts.

In order to increase the efficiency of treatment of the prostate tissue generally, and the treatment of benign hypertrophy of the prostate (BPH) in particular, several new procedures and devices have been developed. These procedures and devices include the use of a Nd:YAG laser for the coagulation and vaporization of prostate tissue generally referred to as abdominal tissue. In order to use Nd:YAG lasers for treatment of BPH, optical fibers capable of deflecting a Nd:YAG laser energy beam about 70° to about 90° to the axis of the optical fiber (generally known as side-firing fibers) have been developed.

Use of a direct contact laser fiber is discussed in an article entitled "TRANSURETHRAL EVAPORIZATION OF PROSTATE (TUEP) WITH Nd:YAG LASER USING A CONTACT FREE BEAM TECHNIQUE: RESULTS IN 61 PATIENTS WITH BENIGN PROSTATIC HYPERPLASIA" by Perinchery Narayan, M.D., George Fournier, M.D., R. Indudhara, M.D., R. Leidich, M.D., K. Shinohara, M.D. and Alex Ingermann, M.D. which appeared at pages 813 through 820, in the June, 1994, Volume 43, Number 6, Issue of Urology (the "Narayan et al. Reference"). The Narayan et al. Reference discusses the use of laser surgery for BPH as a promising alternative to traditional TURP. The Narayan et al Reference discloses that in prostate surgery tissue evaporization referred to as Transurethral Evaporization of Prostate Tissue ("TUEP") was achieved by holding the laser fiber in contact with the area to be treated. The TUEP was performed using an ULTRALINE Laser Fiber manufactured by Heraeus LaserSonics, Milpitas, Calif. The ULTRALINE Laser Fiber uses a 600 microns internal reflector fiber covered by a quartz glass cap that reflects the Nd:YAG beam at 80 degrees to the fiber axis. This fiber transmits a high-power density beam (spot size of 700 micron and divergence of 17 degrees, giving a power density at 60 watts to 80 watts of 16,000 to 21,000 $W/cm^2$) 1 mm from the fiber tip. A 23 French cystoscope (CIRCON ACMI, Stamford, Conn.) equipped with an 8 French laser bridge and a continuous flow system was used for the procedure.

The results as stated in the Narayan et al. Reference was as follows:

" . . . Tissue evaporation was achieved by holding the laser fiber in contact with the area to be treated, and by dragging at a rate of 1 cm/20 seconds of laser energy delivery. At the beginning of each furrow dragging was commenced one bulling was seen indicating tissue evaporation. Dragging the fiber at a rate of 1 cm/20 seconds resulted in a furrow 5 to 7 mm deep with a 3 to 4 mm rim of coagulated tissue immediately next to it."

Another known prior art device for treatment of prostate tissue was presented at a poster session at the Society of Minimal Invasive Therapy ("SMIT") on Nov. 5, 1993. The poster session was entitled "TRANSURETHRAL VAPORIZATION OF THE PROSTATE (T.V.P.): NEW HORIZONS" by Irving M. Bush, M.D., Edward Malters, M.D. and Jan Bush, R.N. (the "Bush et al. Reference") disclosed the use of an improved scored ball produced by CIRCON ACMI Division of Circon Corporation, assignee of the present patent application, with a continuous flow resectoscope for providing transurethral desiccation (vaporization) of the prostate.

The Bush et al Reference states as follows:

"T.U.D (transurethral desiccation of the prostate) was first described in 1874 by Bottini. Since 1966 we have used this visually controlled exact vaporization of the prostate in over 500 men with benign hypertrophy, cancer and bladder neck disease.

In the present method (T.V.P., transurethral vaporization of the prostate) a grooved ball electrode and pure electrosurgical cutting current is used to sculpt out the prostatic bed. T.V.P. has the advantage that it causes little or no bleeding, fluid absorption or electrolyte imbalance. Since the residual desiccated tissue (adequate for pathologic review) is removed at the end of the procedure, there is no slough or delayed bleeding (open vessels are closed without retraction). The patient can leave the hospital, voiding (76%) within the 23 hour observation time in most instances. A new improved scored ball loop (A.C.M.I.) to be used with a continuous flow resectoscope has become available.

T.V.P. is a short procedure without sphincter damage which preserves antegrade ejaculation and has a low (2–3%) subsequent procedure rate. Our experience with the last 100 consecutive patients will be detailed."

For purposes of background in electrosurgical treatment of tissue, there are three basic electrosurgical modes: (a) cutting (dissecting) where tissue is severed by a cutting electrode having a radio frequency ("R.F.") cutting current applied to the cutting electrode and the wounded tissue has a layer of coagulation of about 0.5 mm to about 1 mm beyond the cutting area; (b) fulguration where a ball electrode is positioned above the tissue to be treated and an R.F. arc coagulating current flashes from the ball electrode to the tissue to be treated coagulating the tissue; and (c) desiccation where a smooth ball electrode is held in direct contact with the tissue to be treated and a coagulating current of a selected magnitude is applied to the ball electrode vaporizing the tissue.

The first use of electrosurgical generator for prostatic resection using only an R.F. cutting current was in 1931, and the electrosurgical generator was a McCarthy Surgical Unit Type 504A sold by the Comprex Oscillator Corporation (the "McCarthy Surgical Unit"). The McCarthy Surgical Unit was a highly efficient vacuum tube generator producing sustained oscillation of high frequency.

The McCarthy Surgical Unit was capable of being used for numerous procedures including prostatic resection. The McCarthy Surgical Unit manual states the following with respect to prostatic resection:

"With the wide interest shown in the relief of prostatic encroachment by the intravesical route, we offer this apparatus as the only present day means for actuating some of the electrodes used for this purpose. The splendid action of this current in a liquid medium has eliminated the hazard of failure at the current source.

The method advocated by Dr. Joseph F. McCarthy, for whom this apparatus was designed, permits great flexibility and with proper technique, the entire prostatic urethra can be remodeled.

The Stern Resectoscope under the able guidance of Dr. T. M. Davis has been modified for greater durability and effectiveness. Other surgical methods that have required the use of high frequency currents have been spurred to new activity.

Here again the requirements have been fully and adequately met and an excess of power provided that will encourage continued research. Those engaged in this specialty are freed of the limitations imposed by generators hitherto available.

In the practice of urology the McCarthy Unit provides every modality. Every purpose which requires the use of high frequency current is served; fulguration of cysts, papillomata, tumors, etc., coagulation control of bleeding, resection and treatment.

The current supplied by the type 504-A unit although very efficacious in resection, shows no effect on delicate insulating materials, greatly prolonging the useful life of urological instruments and electrodes. The selective foot switch permits hemorrhage control with the same electrode used for resection, without the necessity of changing the controls on the apparatus."

The McCarthy Surgical Unit manual states that the McCarthy Surgical Unit can be used for coagulation as follows:

"The unit generates by one type of current, and the controls merely provide the means for adjusting its intensity. It has been established that the same current that shows such admirable cutting characteristics is also the most effective for coagulation. By virtue of its penetrating quality the time necessary for coagulating tumor masses or malignancies has been greatly reduced. Sections of coagulated areas show a tapering off into unaffected tissue that practically eliminates the possibility of secondary hemorrhage. Tumor masses show a remarkable shrinkage during application, proportional to their fluid content.

The technique used in coagulation with this type of current is the same as used for tissue destruction and for hemorrhage control. The electrode must be placed in contact with the area to be treated before the current is turned on. After treatment the current must be off before the electrode is removed. No attempt should be made to ply the area with sparks. In following this technique there is no possibility of carbonization, and no tissue can adhere to the electrode."

The McCarthy Surgical Unit utilized for coagulation and dissication a smooth ball shaped electrode having a 3/16 inch (4.5 mm) diameter.

The McCarthy Surgical Unit utilized a control panel having two dials. The first dial was referred to as the Range Selector (R.S.) having three ranges, a low, medium and high, each representing one third of the current output. The second dial was referred as the Current Intensity Control (C.I.C.) and provided smooth linear adjustment over each range. Thus, the Range Selector was a course adjustment and the Current Intensity Control was a fine adjustment. The only current produced by the McCarthy Surgical Unit was a cutting current. The maximum current was in the order of 2,600 milliamperes.

In the McCarthy Surgical Unit, for all operative work, dissection, coagulation, bladder fulguration, prostatic resection and the like, a plate electrode was placed under the patient and connected to an indifferent, terminal which is usually a ground terminal, to ground the patient.

In using the McCarthy Surgical Unit for prostatic resection, bleeding resulting from the removal and vaporization of tissue using high intensity cutting current was controlled by passing the same electrode over the same treated tissue area using a low intensity cutting current for providing coagulation of the treated tissue.

Typically, the resulting coagulation layer of the heated tissue had a thickness in the order of 0.5 mm to about 1 mm which appeared sufficient to stop bleeding.

The following U.S. Patents disclose apparatus having electrosurgical electrodes: U.S. Pat. No. 5,395,363; U.S. Pat. No. 4,917,082; U.S. Pat. No. 4,765,331; U.S. Pat. No. 4,532,924; U.S. Pat. No. 4,314,559; U.S. Pat. No. 4,095,601; and U.S. Pat. No. 642,849.

U.S. Pat. No. 5,395,363 discloses an apparatus for facilitating diathermy coagulation or ablation of tissue by the application of an electrical current to tissue. The apparatus is electrically connected to an electrosurgical generator and has both monopolar and bipolar embodiments. The apparatus includes a roller electrode, as the active electrode, having a plurality of discrete electrical discharge points. The plurality of discharge points is provided by diamond knurling the exterior surface of the active electrode providing a plurality of distinct points for current discharge, facilitating evenly distributed current through the tissue.

U.S. Pat. No. 4,917,082 discloses an electrode for use with urological endoscopes. The electrode comprises an electrode lead, an electrode end and an electrode stabilizer. In the preferred embodiment, the active electrode is a cutting loop used to perform transurethral resection of the prostate ("TURP"). FIG. 5E of U.S. Pat. No. 4,917,082 discloses an alternative embodiment of an electrode wherein the electrode tip 22 comprises a roller electrode having a smooth outer surface.

U.S. Pat. No. 4,765,331 discloses an electrosurgical probe for use in treatment of tissue. The probe includes an active member which is generally cylindrical and has a peripheral surface on which are mounted a plurality of electrodes. The electrodes are mounted such that an electrode of one polarity is interposed with those of the opposite polarity. The length of the electrode can be chosen to obtain desired longitudinal focusing.

U.S. Pat. No. 4,532,924 discloses a multipolar electrosurgical device and method. The device is in the form of an insulative probe body, which is sized to pass through a channel of the endoscope. The probe body is provided with electrically separate conductors which are formed of a plurality of electrodes distributed over the peripheral surface of the probe body. The electrically separate conductors are so sized in width W and spaced from each other by a distance S as to establish a ratio of W:S which enables effective bipolar orientation relative to tissue. In the preferred embodiment, a plurality of six electrodes are aligned longitudinally on the probe body and are used to form six bipolar electric fields.

U.S. Pat. No. 4,614,559 discloses a conductive non-stick electrode for use with a hemostatic tissue cutting scalpel. The scalpel has a first layer of conductive material having a textured working surface for contacting tissue and a second coating of non-stick material deposited on the first layer at least partially filling the textured surface.

U.S. Pat. No. 4,095,601 discloses an electrotherapeutic apparatus having a handle and roller shaped electrode for applying direct current voltage pulses for electrotherapeutic treatment. The roller shaped electrode has a surface that is composed of substantially pyramid shaped parts. the pyramids can either be arranged in rows oriented along surface lines or can be arranged in rows which are offset. In the arrangement where the rows of pyramids are offset, the tips of the pyramids are always located in the center between geometric tips of one pyramid to the tips of the neighboring pyramid in adjacent rows and the spacing is in the order of 6.955 mm. The pyramids do not have a geometric tip, but rather a flattened tip in the form of a square of an edge or side length amounting to 0.5 mm.

U.S. Pat. No. 642,849 discloses an electrical passage instrument which includes smooth, current applying rollers. The rollers are made of carbon and are electrically separated from each other by an insulation.

SUMMARY OF THE INVENTION

A novel, new and unique electrode for a resectoscope for performing tissue resection procedures is disclosed and taught by the present invention. In the preferred embodiment, the electrode comprises an electrode lead member having an elongated conductor member having a first end and a second end with an insulative cover extended therebetween. The first end of the electrode member has a protruding electrode which is adapted to be electrically connected to an electrosurgical generator. The second end of the electrode member terminates in an active member.

The electrode includes an electrode support member operatively connected to the loading member and includes an elongated semi-rigid bifurcated arm terminating in a conductive core spaced a predetermined distance from the active member. The electrode support member has a shaped conductive core electrode member having an opening extending therethrough for rigidly mounting the shaped conductive core electrode member on the conductive core. In the preferred embodiment, the shaped conductive core electrode member is in the form of an elongated curved sharp leading cutting edge which extends toward the bifurcated arm.

Also, a method for treating tissue is shown. The method comprises the steps of: (i) inserting a sheath having an obturator into a urethra; (ii) removing the obturator leaving the sheath in the urethra; (iii) inserting into a resectoscope working element a telescope and an electrode wherein the electrode has an electrode lead member which includes an elongated conductor member having a first end and a second end with an insulative cover extended therebetween wherein said first end has a protruding electrode adapted to be electrically connected to an electrosurgical generator and wherein said second end terminates in an active member and having an electrode support having an elongated semi-rigid bifurcated arm terminating in a conductive core spaced a predetermined distance from the active member and wherein the electrode support member has a shaped conductive core electrode member having an opening extending therethrough for rigidly mounting the shaped conductive core electrode member on the hub; (iv) passing the resectoscope working element having the telescope and electrode mounted thereon into the sheath and visually positioning the shaped conductive core electrode member in the proximity of the tissue to be treated; (v) irrigating through the sheath the tissue to be treated with an irrigation fluid; and (vi) applying an electrosurgical cutting current to said shaped conductive core electrode member at a selected voltage level of between about 200 volts to about 300 volts and moving the shaped conductive core electrode member having an electrosurgical cutting current applied thereto through the tissue to be treated to resect, ablate and coagulate the tissue.

Each of the known prior art devices and method have certain disadvantages.

In performing TURP procedures, a urological procedure using state-of-the-art cutting loop electrodes, the potential of undesirable side effects on the patient such as incontinence and the required use of a foley catheter for a relatively long period of time after the operative procedure, say in the order of 4 to 5 days or more, are becoming objectionable.

The use of laser fibers for treatment of prostatic tissue appears to have less traumatic effect on the patient. However, the efficiency of the procedure in terms of quantities of tissue removed, the technique for using the laser fibers, energy required in joules for vaporizing tissue and the resulting depth of the coagulated layer of tissue are deemed to be shortcomings to the potential long term use of laser fibers for laser prostatectomy.

The use of a scored roller electrode in a resectoscope for treatment of prostatic tissue using cutting current R.F. signals appeared to show that a scored roller ball electrode would successfully vaporize prostatic tissue. However, the removal rate of tissue and therefore, the time required for completion of a procedure appeared to require significant improvement to increase the efficiency of the procedure relative to a laser fiber used for a similar procedure.

Therefore, the problem with the known prior art devices is that the operable power levels in terms of watts are higher than desired using a standard roller ball or a scored roller ball, the size of the craters of vaporized tissue formed in a unit of time is below the desired time verses vaporization results of tissue treatment, the time required to produce trenches of vaporized tissue is longer than desired and the thickness of remaining coagulated tissue is thinner than desired and requires additional coagulating time to develop a sufficient thick coagulate layer of tissue in the area of the treated vaporized tissue.

The shaped conductive core electrode member of the present invention overcomes several of the problems associated with prior electrodes and devices. The preferred embodiment of the present invention is in the form of a shaped conductive core electrode member which has an elongated curved sharp leading cutting edge which is capable of resecting, vaporizing, and coagulating tissue. Further, tissue sections or "tissue chips" can be cut from the tissue mass and be used for pathological examination to determine if the tissue is benign or cancerous. The sharp leading cutting edge forms an elongated area of high current density when an R.F. electrosurgical current is applied to the shaped conductive core electrode member. This enables the shaped conductive core electrode member 52 to mechanically and electrosurgically cut tissue due to the sharp leading cutting edge.

One advantage of the present invention is that the electrode having the shaped conductive core electrode member can be used with standard urological and gynecological resectoscopes.

Another advantage of the present invention is that the shaped conductive core electrode member may have one or more transverse openings extending through the member to produce regions of high current density as well as to allow vaporized material to leave the operative site through the openings. When an R.F. electrosurgical cutting current is applied to the shaped conductive core electrode member, the unique curved sharp leading cutting edge configuration causes areas of high R.F. current concentration or density which provides highly desirable deep tissue penetration. It is desirable for the electrode configuration to have large high current density areas to facilitate deep coagulation of tissue.

Another advantage of the present invention is that the use of a leading cutting edge which maximize R.F. current concentration facilitate reduced power requirement, lower power settings on the electrosurgical generator and improved efficiency. In addition, zones of the electrode may be alternatively coated with an insulating media so as to concentrate the electrosurgical effect in the underlying tissue to achieve maximum hemostasis.

Another advantage of the present invention is that the shaped conductive core electrode member may have polished or treated surface which minimizes tissue sticking or adhesion. Thus, as the shaped conductive core electrode member is moved over and through tissue during treatment, the absence of tissue adhering to the surface of the sharp leading cutting edge or the sides of the shaped conductive core electrode member is desirable to maintain efficiency of vaporization as well as good vision for the surgeon.

Another advantage of the present invention is that the structure of the shaped conductive core electrode member is less atraumatic in the non-energized mode relative to the energized mode.

Another advantage of the present invention is that the shaped conductive core electrode member may be used in urological procedures, gynecological or other procedures requiring tissue vaporization.

Another advantage of the present invention is that the shaped conductive core electrode member can be used with a resectoscope in performing prostatectomy for treatment of BPH of the prostate and for treating bladder tumors.

BRIEF DESCRIPTION OF THE DRAWINGS

These and other advantages of the invention will be readily apparent when considered in light of the detailed description hereinafter of the preferred embodiment and of the drawings which include the following figures.

DESCRIPTION OF THE PREFERRED EMBODIMENT

Figure 1:
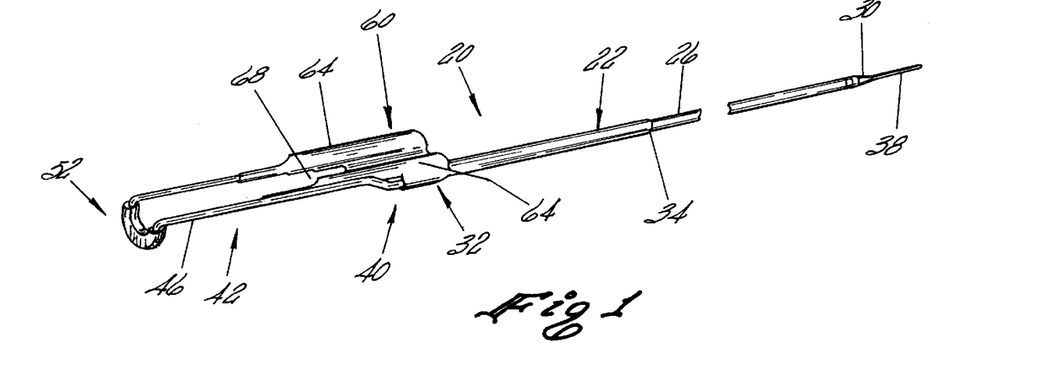
FIG. 1 is a top, front and left side perspective view of a shaped conductive core electrode member having a blade-like leading cutting edge for use with a resectoscope.
Figure 2:
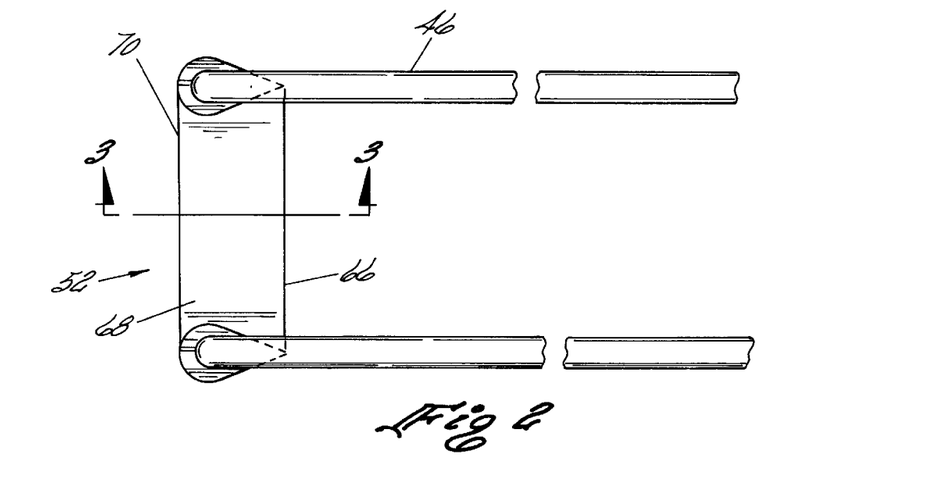
FIG. 2 is a top elevational view showing in greater detail the structure of the shaped conductive core electrode member having a blade-like cutting edge and bifurcated arm.

In the perspective view of FIG. 1, the shaped conductive core electrode member electrode is shown generally as 20. As shown in FIG. 2, the preferred embodiment has a sharpened blade-like leading cutting edge 66. The structure of the electrode is for use with a resectoscope.

As illustrated in FIG. 1, the electrode 20 includes an electrode lead member 22 having an elongated conductor member 26 having a first end 30 and a second end 32. An insulative cover 34 extends between the first end 30 and the second end 32.

The first end 30 has a protruding electrode 38 which is adapted to be electrically connected to an electrosurgical generator. The second end 32 terminates in an active member or a loading member shown generally as 40.

The active member 40 has an electrode support member, shown generally as 42, operatively connected to the loading member 40. The electrode support member 42 has an elongated semi-rigid bifurcated arm 46 which terminates in a conductive core 50 (illustrated in FIG. 3) spaced at a predetermined distance from the active member 40. The bifurcated arm 46 has an insulative covering formed thereon except in the portion thereof which forms the conductive core 50.

The electrode support member 42 has a shaped conductive core electrode member shown generally 52 having an opening 54 (shown in FIGS. 3 and 4) extending therethrough for rigidly mounting the shaped conductive core electrode member 52 on the conductive core 50.

In the preferred embodiment, the electrode stabilizer 60 for stabilizing the shaped conductive core electrode member 52 is proximate a distal region of a telescope mounted in a resectoscope working element. It is envisioned that the electrode 20 does not need to have the electrode stabilizer 60 in order to practice this invention. The distal end of a telescope shown by dashed line 62 is removably supported by stabilizer 60. The stabilizer 60 has a pair of support arms 64 which define a hollowed out space 68 to receive a telescope.

Figure 3:
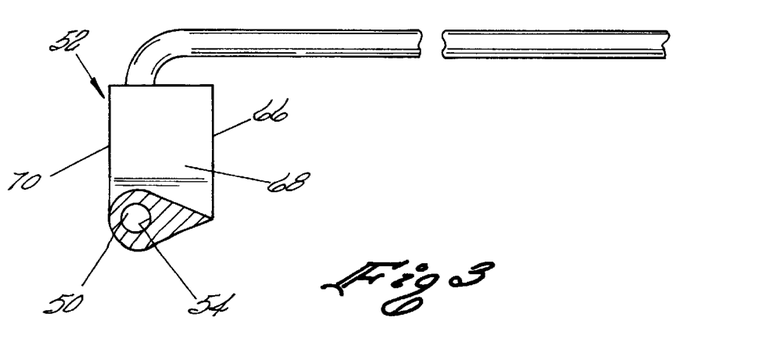
FIG. 3 is a cross-sectional view taken along section lines 3—3 of FIG. 2.

FIGS. 2 and 3 depict the structure of the preferred embodiment of the shaped conductive core electrode member 52 in the form of a sharp leading cutting edge 66. The shaped conductive core electrode member 52 includes a side wall portion 72 and an opposed blunt shaped surface 70. The conductive core 50 extends through the central opening 54 located in the shaped conductive core electrode member 52. The bifurcated arm 46 extends toward the protruding electrode 38.

Figure 4:
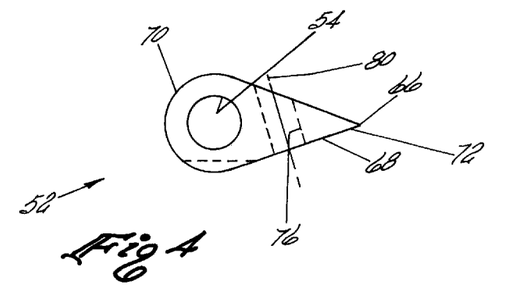
FIG. 4 is a cross-sectional view of another embodiment of a shaped conductive core electrode member having at least one opening extending transversely through the side walls of the shaped conductive core electrode member and with grooves formed in the side wall of the member.

FIG. 4 shows in greater detail the structure of the shaped conductive core electrode member 52 wherein at least one opening 76 is formed cutting through the side wall portion 72. In the embodiment illustrated in FIGS. 2 through 4, the blunt shaped end 70 is smooth. However, as discussed herein below in connection with FIGS. 8 through 11, another embodiment utilizes grooves formed in the side wall portion 72, or wherein the grooves extend around the blunt shaped end 70.

Figure 5:
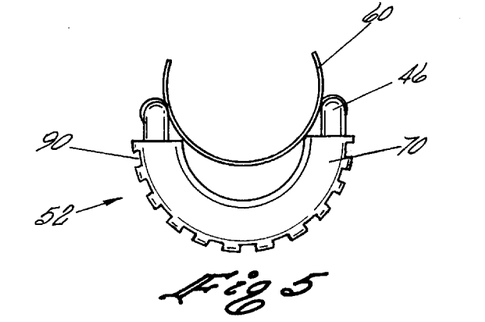
FIG. 5 is a left elevational view of an electrode assembly having a stabilizer.

FIG. 5 depicts in the left side elevational view the structure details of the electrode assemblies showing the electrode stabilizer 60, and the relationship thereof to the bifurcated arm 46 and the shaped conductive core electrode member 52.

Figure 6:
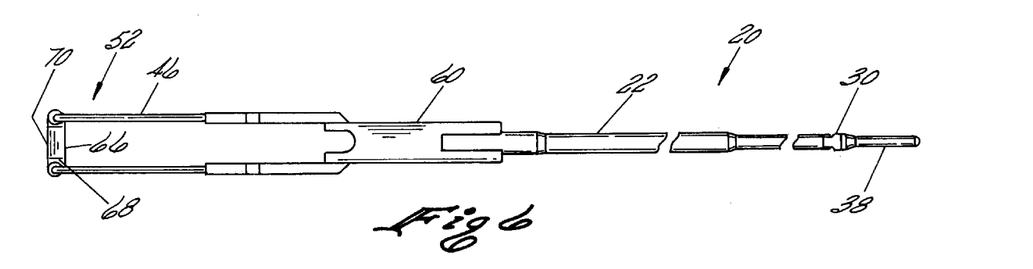
FIG. 6 is a top plan view of an electrode assembly having a shaped conductive core electrode member and an electrode stabilizer.
Figure 7:
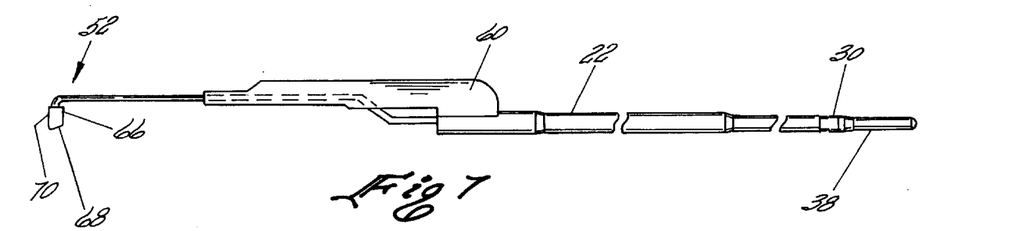
FIG. 7 is a front elevational view of the electrode assembly of FIG. 6.

FIGS. 6 and 7 show the entire electrode assembly 20 and shows that the orientation of the sharp leading cutting edge 66 of the shaped conductive core electrode member 52 extends toward the bifurcated arm 46. In the preferred embodiment, the plane of the sharp leading cutting edge 66 is positioned substantially perpendicular to the direction of cutting. However, it is envisioned that the sharp leading cutting edge 66 could be positioned at a slight angular bias of ±20° to this perpendicular position.

Figures 8, 9:
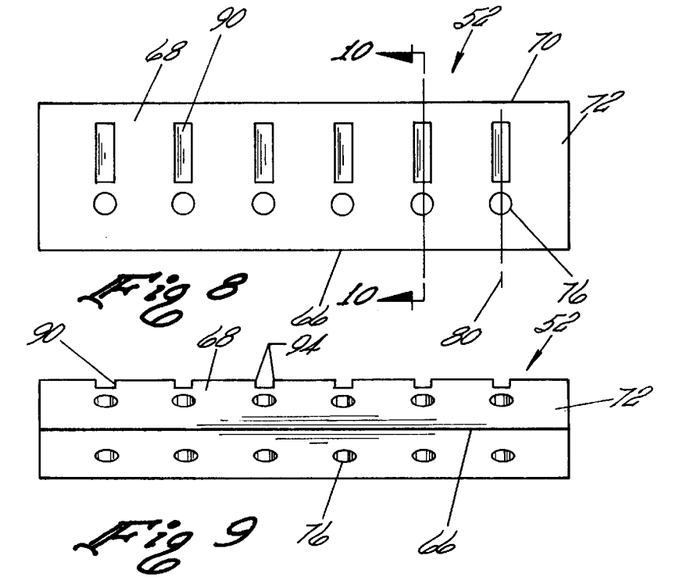
FIG. 8 is a pictorial representation of another embodiment of a shaped conductive core electrode member having a plurality of transverse openings and a plurality of rectangular shaped ridges or grooves located on a portion of the periphery of the angular shaped end of the shaped conductive core electrode member.
FIG. 9 is a front elevational view of the embodiment of the shaped conductive core electrode member illustrated in FIG. 8 showing the rectangular shaped grooves.
Figure 10:
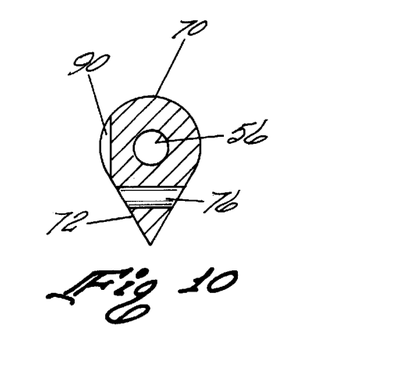
FIG. 10 is a cross-sectional view taken along section lines 10—10 of FIG. 8 wherein the shaped conductive core electrode member has a plurality of openings and a plurality of rectangular shaped ridges or grooves located around the periphery of the angular shaped end of the shaped conductive core electrode member.

FIGS. 8, 9 and 10 depict another embodiment of a shaped conductive core electrode member for practicing this invention. In FIGS. 8, 9 and 10, the shaped conductive core electrode member 52 is illustrated to include the plurality of holes 76 through side walls portion 72 located between the cutting edge 66 and blunt shaped end 70. It is envisioned that the orientation of the openings could be at different selected angles, such as for example perpendicular to one of the side walls 72. In addition, the embodiment illustrated in FIGS. 8, 9 and 10 include a plurality of substantially parallel spaced rectangular shaped ridges or grooves 90 which are located in the side wall portion 72 as illustrated in FIGS. 8, 9 and 10, the ridges or grooves 90 do not extend around the blunt shaped end 70.

As illustrated in FIG. 9, the ridges or grooves 90 have sharp edges illustrated as 94 which function as areas of higher current densities for R.F. electrosurgical current applied to the electrode 20. Specifically, electrosurgical current densities are larger at the sharp edges 94 which enable the shaped conductive core electrode member 52 to effectively coagulate tissue and reduce bleeding during the procedure. Note that FIGS. 8 and 9 show the electrode 52 in its straight form prior to being formed into its final arc-shaped form.

In the preferred embodiment, the typical depth of the ridges or grooves 90 would be in the order of 0.008 inches (0.20 mm) to about 0.015 inches (0.38 mm) and the width of the ridges or grooves would be in order of about of 0.010 inches (0.25 mm) with a spacing between grooves in order of about 0.010 inches (0.25 mm) making the pitch thereof to be approximately thereof 0.020 inches (0.5 mm). The width of the shaped conductive core electrode member 52 as measured from the sharp leading cutting edge 66 to the blunt shaped end 70 would be in the order of about 0.075 inches (2 mm). The opening 76 would have a diameter in the order of 0.016 inches (0.4 mm).

Figures 11, 12, 13:
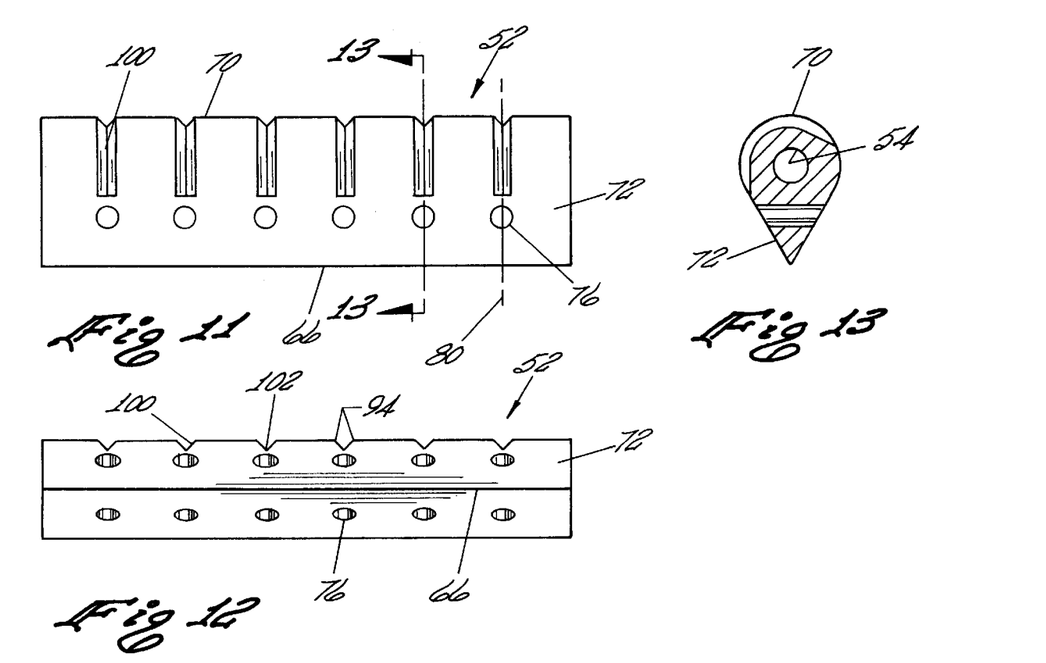
FIG. 11 is a front elevational view of the embodiment of the shaped conductive core electrode member wherein the ridges or grooves are V-shaped.
FIG. 12 is a front elevational view of the embodiment of the shaped conductive core electrode member illustrated in FIG. 11 wherein the ridges or grooves are V-shaped.
FIG. 13 is a cross-sectional view taken along section lines 13—13 of FIG. 11 wherein the shaped conductive core electrode member has a plurality of openings and a plurality of "V"-shaped ridges or grooves located around the periphery of the angular shaped end of the shaped conductive core electrode member.

FIGS. 11, 12 and 13 depict another embodiment of a shaped conductive core electrode member 52 wherein ridges or grooves 100 extend from the side wall portion 72 and around the circumference or outside surface of the blunt shaped member 70. As illustrated in FIG. 11, the ridges or grooves 100 are V-shaped as illustrated by edge 102, however they could also be square shaped or radius shaped. The "V"-shaped ridges or grooves 100 have sharp edges 94 to develop increased current densities in the same manner as discussed above with respect to FIGS. 8, 9 and 10.

FIGS. 14(a), 14(b), 14(c) and 14(d) illustrate the steps of a method for forming a dielectric coating on a selected surface of a shaped conductive core electrode member 110.

Figure 14A:
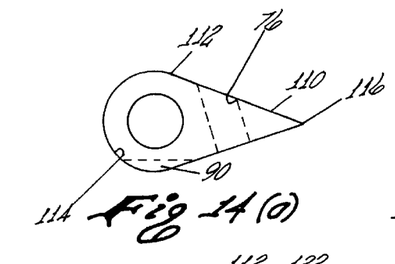
FIGS. 14(a), 14(b), 14(c) and 14(d) are pictorial representations of steps of a process for coating a selected area of a shaped conductive core electrode member with a dielectric coating.

In FIG. 14(a) the shaped conductive core electrode member 110 has a top surface 112 and a bottom surface 114. The shaped conductive core electrode member 110 has, in this embodiment, a sharp leading cutting edge 116. As illustrated in FIG. 14(a), the openings 76 and plurality of substantially parallel spaced rectangular shaped ridges or grooves 90 have been fabricated or formed into the shaped conductive core electrode member 110. Preferably, this step is done before the application of the dielectric material and is referred to by the step of forming the openings 76 and plurality of substantially parallel spaced rectangular shaped ridges or grooves 90 into the shaped conductive core electrode member 110.

Figure 14B:
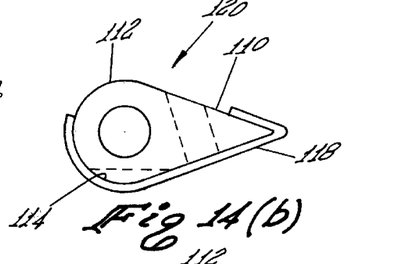

The next step, as illustrated in FIG. 14(b), is the step of forming a mask or resist layer of material, depicted by mask 118, over the surface areas of the shaped conductive core electrode member 110. The surface areas which are masked are those surface areas not to have the dielectric material affixed thereto.

In the embodiment illustrated in FIG. 14(b), the surface areas of the shaped conductive core electrode member 110 which are not to have the dielectric material affixed thereto are the sides and bottom surface of the shaped conductive core electrode member 110. In the step of forming the mask, a selected section or area of the top section, shown generally by arrow 120, is left exposed or unmasked or uncoated with the resist layer of material.

Figure 14C:
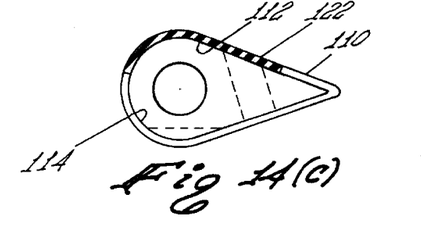

The next step, as illustrated in FIG. 14(c), is the step of affixing onto the exposed top section 120 of the shaped conductive core electrode member 110 a dielectric material having a predetermined thickness. The step of affixing may be accomplished by many techniques known in the art such as, for example, sputtering, vapor deposition, chemical formation or use of other known material depositing techniques.

In FIG. 14(a), the layer of dielectric material is depicted by the cross-sectional insulating layer 122. The thickness of the dielectric material should be in the range of about 5 microns to about 50 microns. The preferred thickness of the dielectric layer is about 25 microns.

The ultimate thickness of the dielectric layer 122 may be obtained by either a single layer of the desired thickness or a plurality of thin layers which, in the aggregate, is substantially equal to the thickness of the dielectric layer 122.

Figure 14D:
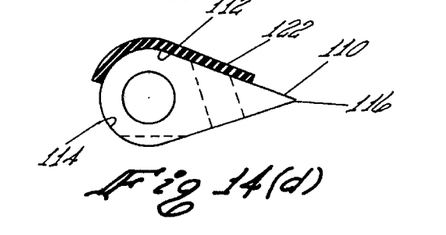

The next step, as illustrated in FIG. 14(d), is the step of removing the mask or resist layer of material depicted by mask 118. This re-exposes the surface areas of the shaped conductive core electrode member 110 which are not to have the dielectric material affixed thereto. In this embodiment, the sides and bottom surface of the shaped conductive core electrode member 110 are re-exposed. This leaves the dielectric material 122 located on and affixed to the selected section or area of the top section 120.

Figure 15:
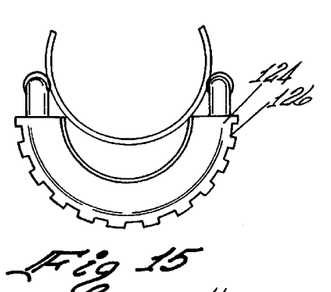
FIG. 15 is a left end elevational view of an electrode assembly having a stabilizer wherein the leading edge of the shaped conductive core electrode has a plurality of sharp teeth members extending toward the bifurcated arm.
Figure 16:
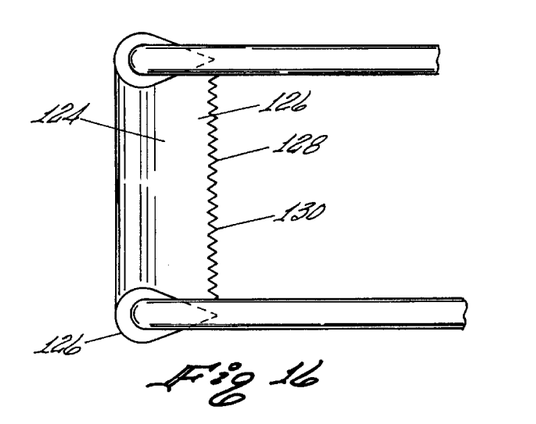
FIG. 16 is a top plan view of the distal end of the electrode assembly showing the shaped conductive core electrode illustrated in FIG. 15.

FIGS. 15 and 16 illustrate another embodiment of a shaped conductive core electrode member 124 having a plurality of rectangular shaped grooves 126 formed in the bottom portion of a shaped conductive core electrode member 124. The shaped conductive core electrode member 124 has a cross-section in the form of a two generally arcuate shaped, sloped intersecting surfaces forming a knife-like leading cutting edge 126 positioned toward the bifurcated arm 46 as illustrated in FIG. 2. the other Generally, the cross-sectional area defined in FIG. 3 is representative of the cross-sectional area of FIG. 16. However, the knife-like leading cutting edge 126 includes a saw tooth cutting edge having a plurality of individual cutting teeth 128. Each individual cutting tooth 128 has a sharp or pointed end 130 which causes high current density when an electrosurgical current is applied to the shaped conductive core electrode member 124.

Figure 17A:
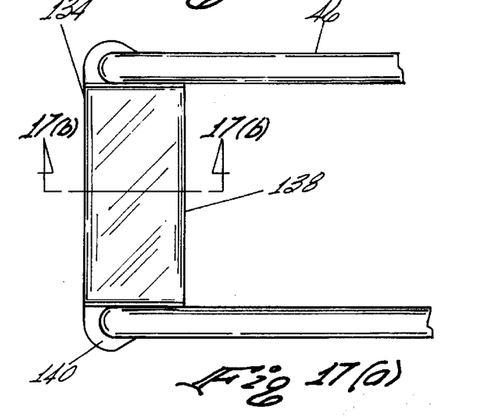
FIG. 17(a) is a top plan view of the distal end of another embodiment of an electrode assembly wherein the shaped conductive core electrode has a substantially planar top surface which is coated with a dielectric coating.
Figure 17B:
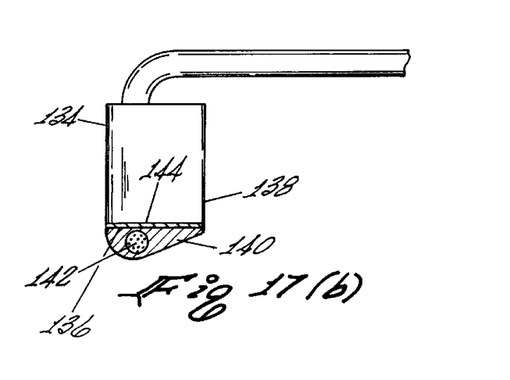
FIG. 17(b) is a cross-section view taken along section lines 17(b)—17(b) of FIG. 17(a) showing the substantially planar top surface and the laminated dielectric coating formed on the surface of the substantially planar top surface.

FIGS. 17(a) and 17(b) illustrate yet another embodiment of a shaped conductive core electrode member 134 which may or may not have a plurality of rectangular shaped ridges or grooves. The ridges or grooves may be similar to rectangular shaped grooves 126 shown in FIG. 15, formed in the bottom portion of a shaped conductive core electrode member 134. In the alternative, the ridges or grooves may be similar to the "V"-shaped ridges or grooves 102 illustrated in FIG. 12.

In the embodiment illustrated in FIGS. 17(a) and 17(b), the shaped conductive core electrode member 124 has a cross-sectional area forming a rounded angular shaped trailing edge 134 and a substantially planer top or lateral surface 138. The substantially planer surface 138 terminates in the knife-like leading cutting edge 138. The knife-like leading cutting edge 138 is formed by two sloped intersecting surfaces. The knife-like leading cutting edge 138 is positioned toward the bifurcated arm 46 as illustrated in FIG. 2.

As illustrated in FIG. 17(b), the cross-sectional area of the electrode 140 is supported by the core 142 which forms part of the bifurcated arm 46. Also, the substantially planer surface 136 is coated with a thin dielectric coating 138. The thin dielectric coating 144 functions to prevent tissue or other material from sticking to or becoming affixed to the shaped electrode 140.

In the alternative, the knife-like leading cutting edge 138 may include a saw tooth cutting edge similar to the saw tooth cutting edge illustrated in FIG. 16 having a plurality of individual cutting teeth 128.

Figures 18, 19, 21:
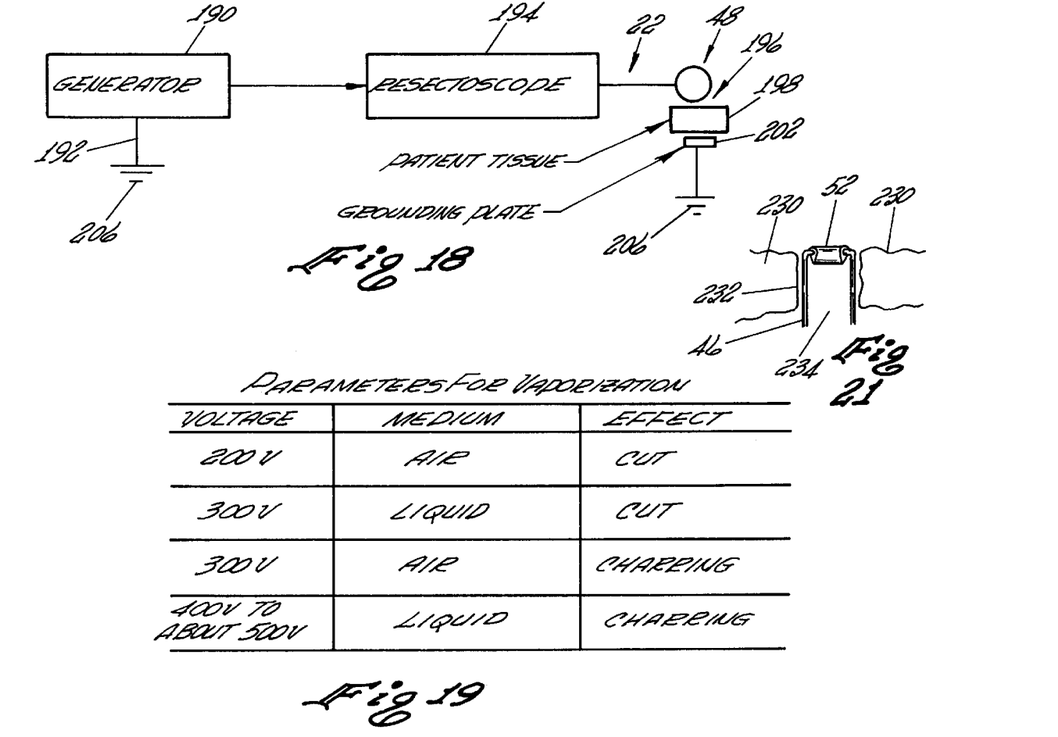
FIG. 18 is a schematic diagram of a resectoscope system using a shaped conductive core electrode member of the present invention for treatment of patient tissue.
FIG. 19 is a chart showing parameters for vaporization.
FIG. 21 is a diagrammatic representation of a trough formed in a patient tissue using a shaped conductive core electrode member of the preferred embodiment of this invention.

FIG. 18 is a schematic diagram of an electrosurgical generator 190 which is operatively connected to a resectoscope 194. The electrosurgical generator 190 produces typical R.F. electrosurgical currents which may be a cutting current, a blend current or a coagulating current. A description of typical R.F. electrosurgical currents is set forth at pages 96 through 97 and page 100 of the ValleyLab SSE4 Instruction Manual.

The electrosurgical current from the generator 190 is applied by the electrode tip 22 to the shaped conductive core electrode member 48 to a patient tissue to be treated, shown by tissue 198.

A dispersive electrode or patient plate, shown as 202, is affixed to the patient, shown by arrow 196, usually by means of a conductive gel. The dispersive electrode 202 is electrically connected to an isolated terminal 206. In order to complete the electrical path back to the electrosurgical generator 190, the electrosurgical generator 190 is electrically connected to the isolated terminal 206.

Thus, the patient including the patient tissue 198 is part of the electrically conductive path. The shaped conductive core electrode member 48 has areas of high concentration of R.F. electrosurgical current which form on the knife-like leading cutting edge, such as for example leading cutting edge 66 illustrated in FIG. 2, and on the protruding ridges or grooves, such as, for example, sharp edges 94 on the rectangular shaped grooves illustrated in FIG. 9 or the sharp edges 94 on the "V"-shaped grooves illustrated in FIG. 12. The sharp points and/or knife-like leading cutting edge of the shaped conductive core electrode member 48, result in areas of increased current density which electrically interact with the tissue being treated. During treatment, the shaped conductive core electrode member 48 is moved slowly through the tissue allowing the shaped conductive core electrode member 48 to electrosurgically cut the tissue, not unlike moving a hot knife through butter, thereby cutting away an elongated chip of tissue and coagulating the remaining tissue forming a trough therein. The chips of tissue can be used for a pathological analysis to determine the status of the tissue, such as for example, whether the tissue is benign or cancerous. In this environment, the shaped conductive core electrode member 48 functions as an active electrode while the patient grounding plate functions as a dispersive electrode.

FIG. 19 shows a table of parameters for vaporization using the teachings of the invention. The procedure can be performed with the shaped conductive core electrode member 48 in either air or liquid as a medium. As shown by the table of FIG. 19, air requires less electrical voltage and power such that an electrosurgical voltage of about 200 volts and a power level of between 160 watts to 240 watts will provide the desired cutting action. An electrosurgical voltage of about 300 volts in air produces charring resulting in a tissue layer having high resistance, which is undesirable.

In liquid, as shown by the table of FIG. 19, an electrosurgical voltage of about 300 volts or higher and a power level of between 160 and 300 watts produces the desired cutting action while an electrosurgical voltage of about 400 volts to about 500 when cutting volts produces charring of the tissue, which is undesirable.

Figure 20:
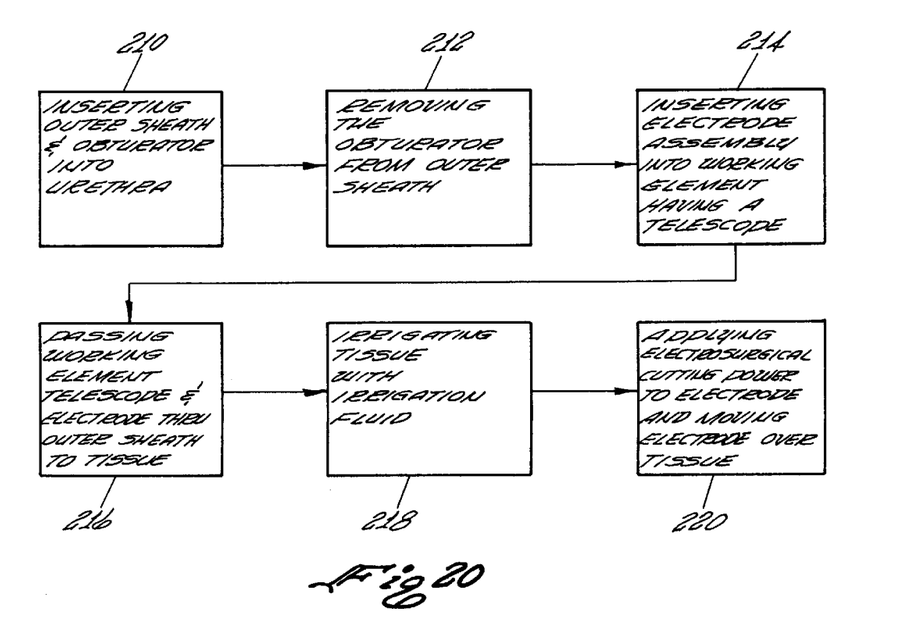
FIG. 20 is a block diagram of a method for using the shaped conductive core electrode member of the present invention in a urological procedure.

A method for treating tissue can be performed using the shaped conductive core electrode member of the present invention. FIG. 20 illustrates the steps of the method. The method comprises the steps of inserting a sheath, which may be an outer sheath for a continuous flow resectoscope (CFR), having a visual obturator into a urethra as shown by step 210.

The step of removing the visual obturator leaving the outer sheath in the urethra is shown by step 212. Step 214 provides for inserting into a resectoscope working element a telescope and an electrode wherein the electrode has an electrode lead member which includes an elongated conductor member having a first end and a second end with an insulative cover extended therebetween wherein said first end has a protruding electrode adapted to be electrically connected to an electrosurgical generator and wherein said second end terminates in an active member and having an electrode support having an elongated semi-rigid bifurcated arm terminating in a conductive core spaced a predetermined distance from the active member and wherein the electrode support member has a shaped conductive core electrode member having an opening extending therethrough for rigidly mounting the shaped conductive core electrode member on the conductive core.

Steps 214 and 216 provide for assembling the resectoscope working element having the telescope and electrode mounted thereon into an inner sheath and then inserting this assembly into the outer sheath and visually positioning the shaped conductive core electrode member in the proximity of the tissue to be treated.

Step 218 provides for irrigating the tissue to be treated with an irrigation fluid.

Step 220 provides for applying an electrosurgical cutting current to the shaped conductive core electrode member at a selected voltage level of between about 200 volts to about 500 volts.

Step 220 also provides for moving the shaped conductive core electrode member having an electrosurgical cutting current applied thereto through the tissue to be treated to resect and coagulate the tissue.

In the preferred embodiment, the method for treating prostate tissue comprises the step of irrigating through an instrument the prostate tissue to be treated and applying a high electrosurgical cutting current to shaped conductive core electrode member at a selected voltage level of between about 200 volts to about 500 volts, and moving the shaped conductive core electrode member having the electrosurgical cutting current applied thereto through a selected portion of prostate tissue to be treated to resect and coagulate the tissue and form a trough having a coagulation layer of treated tissue preferably of at least 2 mm.

FIG. 21 is a pictorial representation of a tissue area shown by 230, such as a prostate, wherein the shaped conductive core electrode member 52 supported by bifurcated arm 46 has formed a crater or trough 234 having side walls 232.

In utilizing the shaped conductive core electrode member 52 as shown in FIG. 21, the velocity of movement of the shaped conductive core electrode member 52 in prostate tissue is approximately 5 mm/sec. The depth of the trough (height of side walls 232) is in the order of about 3 mm.

Figures 22, 23, 24, 25:
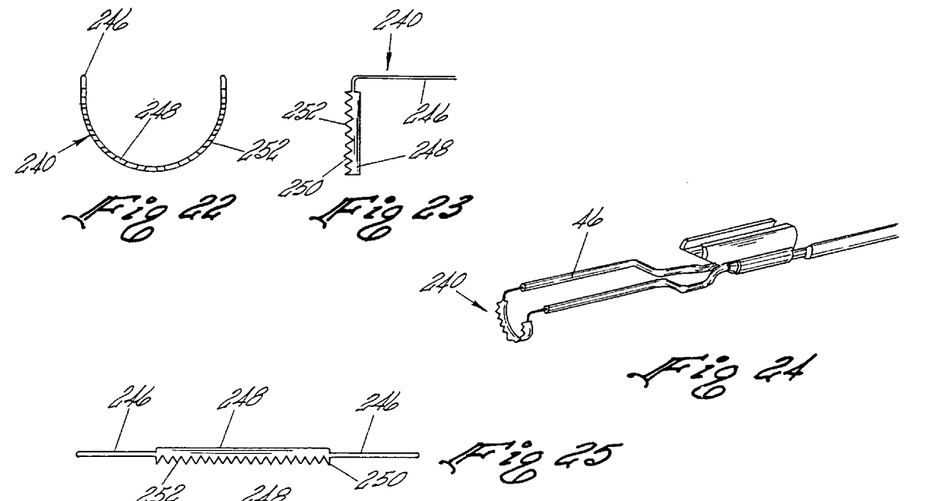
FIG. 22 is a front elevational view of a shaped conductive core electrode member wherein the shaped trailing edge is in the form of a plurality of sharp edges for forming a plurality of areas of high current density when an R.F. electrosurgical current is applied thereto and which extend away from the bifurcated to form a trailing edge for the shaped conductive core electrode member.
FIG. 23 is a sectional view taken along section lines 23—23 of FIG. 22.
FIG. 24 is a front, left end and top perspective view of an electrode of FIG. 22 having the plurality of sharp teeth extending away from the bifurcated arm.
FIG. 25 is a top plan view of the shaped conductive core electrode member prior to forming the electrode and rigidly affixing the same to the bifurcated arms as illustrated in FIG. 22 showing a pair of spaced opposed conducting support leads operatively connected to the shaped conductive core electrode member wherein the width of the shaped conductive core electrode member is greater than the width of the spaced opposed conducting support leads.

FIG. 22 is a front elevational view of FIG. 24, an electrode shown generally by arrow 240 has a pair of opposed conducting support leads 246, shown in FIG. 23, and a shaped conductive core electrode member 248. The shaped conductive core member 248 defines a shaped trailing edge, shown as 250 in FIG. 23, which is in the form of a plurality of sharp edges 252 for forming a plurality of areas of high current density when an R.F. electrosurgical current is applied thereto. The shaped trailing edge in the form of the plurality of sharp edges 252 extend away from the bifurcated arm to form a trailing edge for the shaped conductive core electrode member 248.

The sectional view of FIG. 23 shows that the pair of spaced opposed conducting support leads 246 are deflected or bent in a direction to cause the plurality of sharp edges 252 to extend away from the bifurcated to form a trailing edge for the shaped conductive core electrode member 248.

In the front, left end and top perspective view of FIG. 24, the plurality of sharp teeth 252 which are formed in the leading edge 250 extending away from the bifurcated arm. For purposes of explanation, the electrode 240 is usually used to resect or cut tissue as the electrode 240 is transported by the resectoscope towards the bifurcated arm 46. As such, the shaped leading edge 250 forms the trailing edge of electrode 240 as illustrated in FIG. 27.

Figure 26:
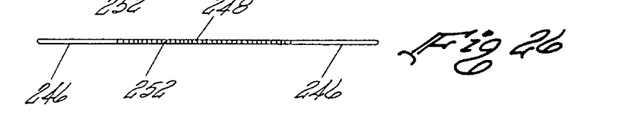
FIG. 26 is a front plan view of the shaped conductive core electrode member illustrated in FIG. 25 showing that the thickness of the spaced opposed conducting support leads is substantially equal to the thickness of the shaped conductive core electrode member.

In FIGS. 25 and 26, the top plan view of the shaped conductive core electrode member 248 is shown prior to forming the electrode and rigidly affixing the same to the bifurcated arms as illustrated in FIG. 22. As illustrated in FIG. 25, the shaped conductive core electrode member 248 has a pair of spaced opposed conducting support leads 246 operatively connected to the shaped conductive core electrode member 248 wherein the width of the shaped conductive core electrode member 248 is greater than the width of the spaced opposed conducting support leads 246.

In FIG. 26, the front plan view of the shaped conductive core electrode member 248 illustrated in FIG. 25 and shows that the thickness of the spaced opposed conducting support leads 246 is substantially equal to the thickness of the shaped conductive core electrode member 248.

Figure 27:
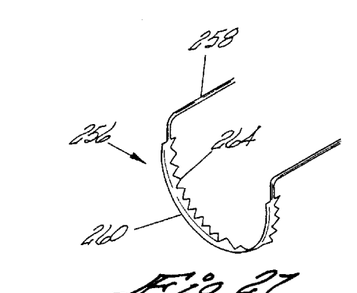
FIG. 27 is a front, left end and top perspective view of another embodiment of an electrode having the plurality of sharp teeth extending towards the bifurcated arm.
Figures 28, 29:
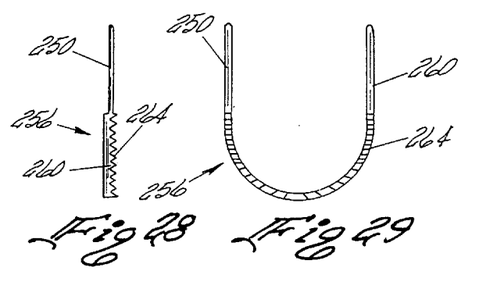
FIG. 28 is a left end elevational view of the embodiment of the shaped conductive core electrode member of FIG. 27 wherein the shaped leading edge thereof is in the form of a plurality of sharp edges for forming a plurality of areas of high current density when an R.F. electrosurgical current is applied thereto and which extends towards the bifurcated arm and to form a shaped leading edge for the shaped conductive core electrode member.
FIG. 29 is a front plan view of the embodiment of FIG. 28.

In FIGS. 27, 28 and 29, another embodiment of an electrode 256 having a pair of spaced opposing conducting support leads 258 and a shaped conductive core electrode member 260. The shaped conductive core electrode member 260 has a plurality of sharp teeth 264 extending towards the bifurcated arm 46 (illustrated in FIG. 1).

As illustrated in FIGS. 27 and 28 the shaped conductive core electrode member 260, the shaped leading edge includes the plurality of sharp edges 264 for forming a plurality of areas of high current density when an R.F. electrosurgical current is applied thereto.

Figure 30:
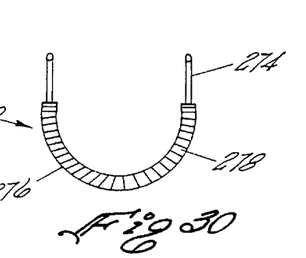
FIG. 30 is a front plan view of another embodiment of a shaped conductive core electrode member showing that the thickness of the shaped conductive core electrode member is greater than the thickness of the pair of the spaced opposed conducting support leads.
Figure 31:
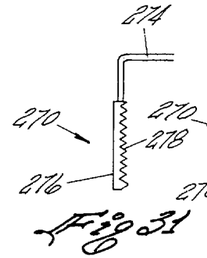
FIG. 31 is a section view taken along section lines 31—31 of FIG. 30.

FIGS. 30 and 31 show another embodiment of an electrode 270 having a pair of spaced opposed conducting support leads 274 and a shaped conductive core electrode member 276. The shaped conductive core electrode member 274 has a plurality of sharp teeth 278 extending towards the bifurcated arm 46 (illustrated in FIG. 1).

FIG. 29 shows that the thickness of the shaped conductive core electrode member 276 is greater than the thickness of the pair of the spaced opposed conducting support leads 274.

In the above described embodiments wherein the shaped leading edge is in the form of an elongated, substantially sharp cutting leading edge or the leading edge is in the form of a plurality of sharp edges, application of an R.F. electrosurgical current to the electrode results in areas of high current density. When the electrosurgical voltage is programmed at a selected voltage level of between about 200 volts to about 500 volts, contacting and moving the vaporizing, cutting and coagulating shaped conductive core electrode member through a selected portion of the tissue to be treated results in the resection and the vaporization of the tissue while forming a coagulation layer in a remaining crater of the treated tissue.

The R.F. electrosurgical setting cooperates with the raised ridges, protrusions, sharp edges or points to form areas of increased current densities which generate sufficient current flow at the appropriate voltage levels to vaporize and coagulate the tissue. The tissue surrounding the vaporized tissue becomes coagulated by the R.F. electrosurgical current at the boundary of the vaporized tissue resulting in a layer of necrosed tissue around the side walls 194 and trough 234 as illustrated in FIG. 21. The thickness of the coagulated layer is in the order of about 1.5 mm to about 2 mm. Energy settings in the range of 160 watts to about 300 watts is desired, with the preferred power settings to be at least 250 watts.

The preferred embodiment shown and described herein is directed for use in a urological procedure. This is an exemplary use and it is envisioned that the principle and teaching herein could be adapted for other procedures.

As an example, the electrode structure could be designed for use in a gynecological procedure with a gynecological resectoscope for performing removal of tissue or debulking myomas.

In addition, the shaped conductive core electrode member could be used as part of instrumentation for use in general surgery and minimally invasive surgery.

Also, various other configurations for the design of the shaped conductive core electrode member are envisioned and the preferred embodiment and species disclosed and described herein are exemplary and are not intended to restrict the invention to the exemplary configuration disclosed herein.

What is claimed is:

1. An electrode comprising
a vaporizing, cutting and coagulating shaped conductive core electrode member having a shaped leading edge and a trailing edge rigidly mounted on an electrode support member, said shaped conductive core electrode member having side walls and the shaped conductive core electrode member has a plurality of openings each of which extends through the side walls and through said shaped conductive core electrode member.

2. An electrode comprising
a vaporizing, cutting and coagulating shaped conductive core electrode member having a shaped leading edge and a trailing edge rigidly mounted on an electrode support member, said shaped conductive core electrode member having a substantially sharp leading edge on one side and a substantially blunt shaped end on a spaced opposed side defining the trailing edge, said shaped conductive core member having a lateral surface extending between the substantially sharp leading edge and the substantially blunt shaped end, said lateral surface and said blunt shaped end having formed thereon a plurality of substantially parallel spaced grooves having substantially sharp edges, and a selected portion of the lateral surface having a thin dielectric coating formed thereon.

3. The electrode of claim 2 wherein the thickness of the thin dielectric coating is in the range of about 5 microns to about 50 microns.

4. The electrode of claim 3 wherein the thickness of the thin dielectric coating is about 25 microns.

5. An electrode comprising
a vaporizing, cutting and coagulating shaped conductive core electrode member having a shaped leading edge and a trailing edge rigidly mounted on an electrode support member, said shaped conductive core electrode member having a substantially sharp leading edge on one side and a substantially blunt shaped end on a spaced opposed side defining the trailing edge, said shaped conductive core member having a substantially planar lateral surface extending between the substantially sharp leading edge and the substantially blunt shaped end, said lateral surface and said blunt shaped end having formed thereon a plurality of substantially parallel spaced grooves having substantially sharp edges, and a selected portion of the substantially planar lateral surface having a thin dielectric coating formed thereon.

6. An electrode for use with a resectoscope comprising
an electrode lead member terminating in an active member;
an electrode support member operatively connected to said active member having an elongated semi-rigid bifurcated arm terminating in a conductive core spaced a predetermined distance from said active member; and
a vaporizing, cutting and coagulating shaped conductive core electrode member having an opening extending therethrough for rigidly mounting said shaped conductive core electrode member on said conductive core, said shaped conductive core electrode member having a substantially sharp leading cutting edge on one side and a substantially blunt shaped end on a spaced opposed side, said shaped conductive core electrode member having side walls and at least one opening which extends through said shaped conductive core electrode member.

7. The electrode of claim 6 wherein the shaped conductive core electrode member has plurality of openings each of which extends through the side walls and through said shaped conductive core electrode member.

8. An electrode for use with a resectoscope comprising
an electrode lead member terminating in an active member;
an electrode support member operatively connected to said active member having an elongated semi-rigid bifurcated arm terminating in a conductive core spaced a predetermined distance from said active member; and
a vaporizing, cutting and coagulating shaped conductive core electrode member having an opening extending therethrough for rigidly mounting said shaped conductive core electrode member on said conductive core, said shaped conductive core electrode member having a substantially sharp leading cutting edge on one side and a substantially blunt shaped end on a spaced opposed side, said shaped conductive core electrode member having a lateral surface extending between the substantially sharp leading cutting edge and the substantially blunt shaped end, said lateral surface and said blunt shaped end having formed thereon a plurality of substantially parallel spaced grooves having substantially sharp edges, and a selected portion of the lateral surface having a thin dielectric coating formed thereon.

9. The electrode of claim 8 wherein the thickness of the thin dielectric coating is in the range of about 5 microns to about 50 microns.

10. The electrode of claim 9 wherein the thickness of the thin dielectric coating is about 25 microns.

11. An electrode for use with a resectoscope comprising
an electrode lead member terminating in an active member;
an electrode support member operatively connected to said active member having an elongated semi-rigid bifurcated arm terminating in a conductive core spaced a predetermined distance from said active member; and
a vaporizing, cutting and coagulating shaped conductive core electrode member having an opening extending therethrough for rigidly mounting said shaped conductive core electrode member on said conductive core, said shaped conductive core electrode member having a substantially sharp leading edge on one side and a substantially blunt shaped end on a spaced opposed side, said shaped conductive core electrode member having a substantially planar lateral surface extending between the substantially sharp leading edge and the substantially blunt shaped end, said lateral surface and said blunt shaped end having formed thereon a plurality of substantially parallel spaced grooves having substantially sharp edges, and a selected portion of the substantially planar lateral surface having a thin dielectric coating formed thereon.

12. An electrode for vaporizing, cutting, or coagulating tissue comprising
a shaped conductive core electrode member mounted on an electrode support member, said shaped conductive core electrode member having a leading edge and a trailing edge, said core electrode member having a lateral surface extending between the leading edge and the trailing edge, at least a selected portion of the lateral surface having a thin dielectric coating formed thereon, said portion with the dielectric coating not being intended for vaporizing, cutting, and coagulating tissue.

13. The electrode of claim 12 wherein the lateral surface is opposed to another surface on the conductive core electrode member intended for contacting tissue to vaporize, cut, and coagulate the tissue, the lateral surface having a portion adjacent the leading edge that is free of said dielectric coating.

14. The electrode of claim 13 wherein at least a selected portion of the trailing edge includes a thin dielectric coating formed therein.

15. The electrode of claim 12 wherein said lateral surface includes a substantially planar surface.

16. The electrode of claim 12 wherein the conductive core electrode member has a tissue contacting surface having at least two edges that function as areas of high current density for RF current applied to the electrode.

17. The electrode of claim 16 wherein the conductive core electrode member has a tissue contacting surface having at least one groove providing said edges.

18. The electrode of claim 12 wherein said electrode has a tissue contacting surface having at least 4 edges that function as areas of high current density for RF current applied to the electrode.

19. The electrode of claim 18 wherein the conductive core electrode member has at least two grooves providing said edges.

20. The electrode of claim 12 wherein said electrode has a tissue contacting surface having at least 6 edges that function as areas of high current density for RF current applied to the electrode.

21. The electrode of claim 20 wherein the conductive core electrode member has at least three grooves providing said edges.

22. An electrode for vaporizing, cutting or coagulating tissue comprising a vaporizing, cutting and coagulating shaped conductive core electrode member having a shaped leading edge and a trailing edge mounted on an electrode support member, said shaped conductive core electrode member having a substantially sharp leading edge on one side and a substantially blunt shaped end on a spaced opposed side defining the trailing edge, said shaped conductive core electrode member having a substantially planar lateral surface extending between the substantially sharp leading edge and the substantially blunt shaped end, and a selected portion of the substantially planar lateral surface having a thin dielectric coating formed thereon.

23. The electrode of claim 22 wherein the thin dielectric coating is about 5 microns to about 50 microns thick.

24. The electrode of claim 22 wherein the conductive core electrode member has at least three grooves on a surface intended for contacting tissue to vaporize, cut, or coagulate the tissue.

25. An electrode for use with a resectoscope comprising an electrode lead member terminating in an active member;

an electrode support member operatively connected to said active member having an elongated semi-rigid bifurcated arm terminating in a conductive core spaced a predetermined distance from said active member; and a vaporizing, cutting and coagulating shaped conductive core electrode member having an opening extending therethrough for rigidly mounting said shaped conductive core electrode member on said conductive core, said shaped conductive core electrode member having a substantially sharp leading edge on one side and a substantially blunt shaped end on a spaced opposed side, said shaped conductive core electrode member having a lateral surface extending between the substantially sharp leading edge and the substantially blunt shaped end, a selected portion of the lateral surface having a thin dielectric coating formed thereon, the lateral surface being opposed to another surface on the conductive core member intended for contacting tissue to vaporize, cut, or coagulate the tissue, the other surface intended for tissue contact having at least two grooves.

* * * * *